United States Patent
Takayama et al.

(10) Patent No.: US 6,373,575 B1
(45) Date of Patent: Apr. 16, 2002

(54) PAPER CLASSIFICATION APPARATUS

(75) Inventors: Satoshi Takayama; Shigeru Machida, both of Kawasaki (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/391,344

(22) Filed: Sep. 8, 1999

(30) Foreign Application Priority Data

Sep. 16, 1998 (JP) .......................................... 10-261395

(51) Int. Cl.$^7$ ................................................ G01B 9/02
(52) U.S. Cl. ........................ 356/445; 355/30; 355/35; 355/39; 356/456; 358/290; 358/301
(58) Field of Search ............................... 356/455, 456, 356/445; 355/30, 35, 39, 403; 358/296, 301

(56) References Cited

U.S. PATENT DOCUMENTS

| | | | |
|---|---|---|---|
| 4,551,008 A | * 11/1985 | Banton | 355/39 |
| 4,573,084 A | * 2/1986 | Iida | 355/296 |
| 4,774,593 A | * 9/1988 | Deguchi et al. | 358/301 |
| 5,922,115 A | 7/1999 | Sano et al. | |

FOREIGN PATENT DOCUMENTS

| | | | |
|---|---|---|---|
| JP | 406233031 | * | 8/1994 |
| JP | 407240814 | * | 9/1995 |
| JP | 09136462 | * | 5/1997 |
| JP | 410023203 | * | 1/1998 |

* cited by examiner

Primary Examiner—Frank G. Font
Assistant Examiner—Sang H. Nguyen
(74) Attorney, Agent, or Firm—Oblon, Spivak, McClelland, Maier & Neustadt, P.C.

(57) ABSTRACT

A paper classification apparatus includes a heater for heating paper or a solvent supply unit for supplying a solvent to the paper, a detector, a computer, and a selector guide. The detector detects the reflection density of the paper after being heated or supplied with the solvent. The computer compares the detected reflecting density of the paper with a predetermined reference value stored in a memory. The selector guide classifies the paper on the basis of a comparison result of the reflection density. This apparatus can classify plain paper having an image formed with an ordinary image forming material, plain paper having an image formed with an erasable image forming material, and thermosensible paper.

18 Claims, 9 Drawing Sheets

PAPER CLASSIFICATION APPARATUS

BACKGROUND OF THE INVENTION

The present invention relates to a paper classification apparatus for classifying paper having an image formed with an image forming material such as common toner or ink, paper having an image formed with an erasable image forming material, and thermosensible paper.

In recent years, along with the advance of office automation, the amount of various types of information has increased considerably, and accordingly information output has also increased. The information outputs are represented by a display output and a hard copy output from a printer to paper. The display output requires a large-scale circuit board in a display unit and accordingly has problems in terms of portability and cost. The hard copy output is the most basic information display means and is excellent in versatility and storability. With the hard copy output, when information increases, a large amount of paper is consumed as a recording medium, leading to an increase in deforestation to provide the paper material. Forest resources are very significant from the viewpoint of sustenance of global environment and suppression of greenhouse effect brought about by carbon dioxide gas. For these reasons, it is a serious issue to minimize any more deforestation and to efficiently utilize the currently available paper resources.

Conventionally, to recycle paper resources, paper printed with an image forming material is processed by using a large amount of bleaching agent and water, and remaking paper having poor paper quality is manufactured from paper fiber. This method leads to a rise in cost of the regenerated paper and another environmental pollution as a result of waste fluid process.

To solve this problem, the present inventors are working on development of an image forming material that contains a color former, a developer, and a decoloring agent having a property to capture the color former or developer, so that it can form an image in the same manner as an ordinary image forming material does, and that image erasure is enabled by processing with heat or a solvent. When such an erasable image forming material is used, paper from which an image is erased to restore the blank state can be reused repeatedly while preventing degradation of the paper quality as much as possible. The paper may be recycled when the paper quality becomes remarkably poor due to reuse. This considerably improves use efficiency of the paper resources. The overall paper use amount can be reduced in this manner to minimize deforestation. In addition, an increase in cost of the regenerated paper and environmental pollution caused by the waste fluid process, which pose problems in the current recycling system, can be avoided as much as possible.

When the erasable image forming material which is under development by the present inventors becomes widely used, waste paper including a mixture of paper printed with a general image forming material, paper printed with an erasable image forming material, and thermosensible paper will be discharged from offices and the like. To reuse or recycle such waste paper including a mixture of these various paper types, paper must be classified in accordance with each individual type.

BRIEF SUMMARY OF THE INVENTION

It is an object of the present invention to provide an apparatus capable of classifying paper having an image formed with a general image forming material, paper having an image formed with an erasable image forming material, and thermosensible paper.

According to an aspect of the present invention, there is provided a paper classification apparatus comprising means for applying an external stimulus that can change a reflection density of paper, means for detecting the reflection density of the paper after being applied with the external stimulus, means for comparing the detected reflection density of the paper with a predetermined reference value, and means for classifying the paper on the basis of a comparison result of the reflection density.

In the present invention, as the means for applying the external stimulus, means for heating the paper or means for supplying a solvent onto the paper is used.

More specifically, the paper classification apparatus according to the present invention has a heater for heating paper or a supply unit for supplying a solvent to the paper, a detector for detecting a reflection density of the paper after being heated or supplied with the solvent, a computer for comparing the detected reflecting density of the paper with a predetermined reference value, and a selector guide for classifying the paper on the basis of a comparison result of the reflection density.

According to another aspect of the present invention, there is provided a paper classification apparatus comprising means for detecting a reflection density of paper, means for applying an external stimulus that can change the reflection density of the paper, means for comparing reflection densities of the paper before and after being applied with the external stimulus, and means for classifying the paper on the basis of a comparison result of the reflection densities.

More specifically, the paper classification apparatus according to the present invention has a first detector for detecting a reflection density of paper, a heater for heating the paper or a supply unit for supplying a solvent to the paper, a second detector for detecting a reflection density of the paper after being heated or supplied with the solvent, a computer for comparing reflecting densities of the paper before and after being heated or supplied with the solvent, and a selector guide for classifying the paper on the basis of a comparison result of the reflection densities.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
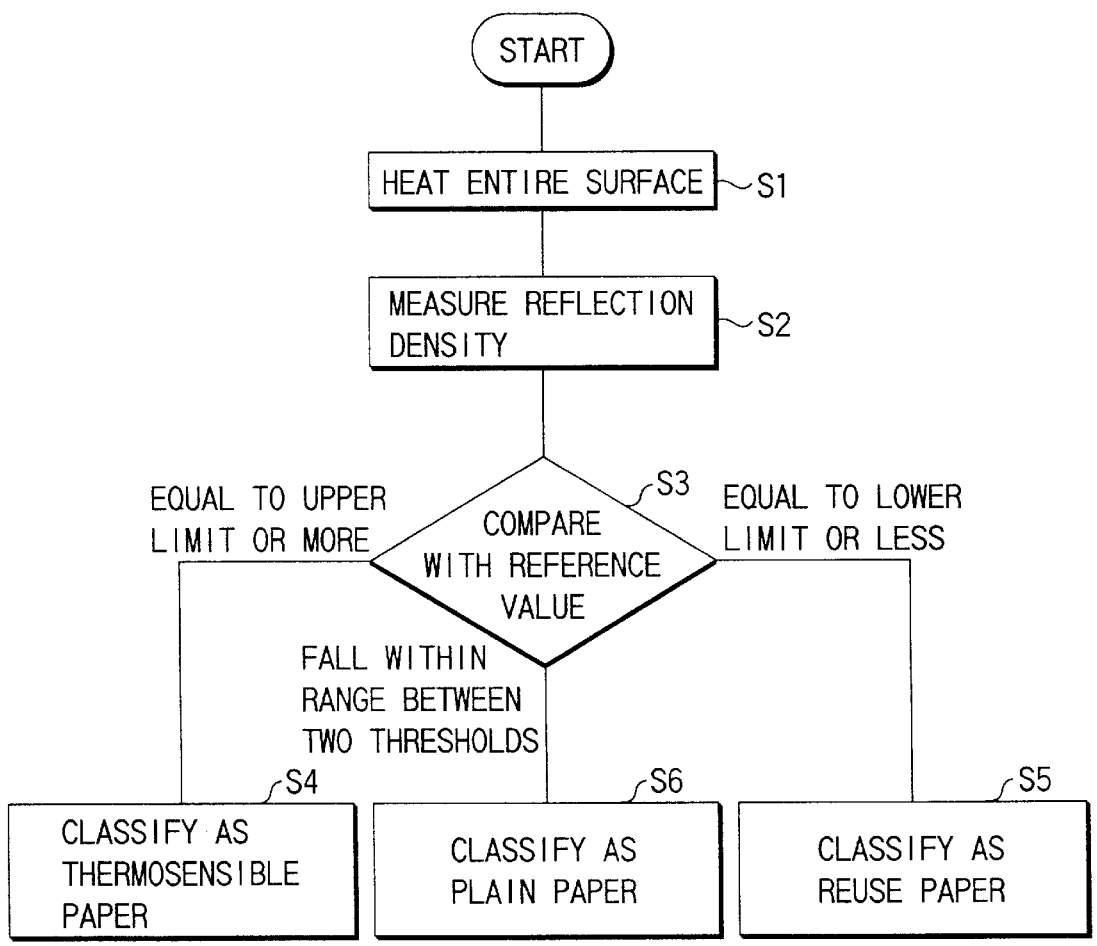
FIG. 1 is a flow chart showing an example of a paper classifying method according to the present invention.

The present invention will be described in detail.

Paper types to be classified by a paper classification apparatus according to the present invention are three, i.e., plain paper having an image formed with an ordinary image forming material (toner or ink), plain paper having an image formed with an erasable image forming material (toner or ink), and thermosensible paper. In addition, transparent sheets used for an overhead projector (OHP) may also be included as a processing object.

The erasable image forming material contains a color former, a developer, and a decoloring agent. As the color former, a leuco dye or the like is typically used. As the developer, an acid compound such as a phenol derivative is typically used. As the decoloring agent, cholic acid, lithocholic acid, and a derivative of cholic or lithocholic acid, and a nonaromatic cyclic compound of a 5-membered ring or more having one or more hydroxyl groups, is used. The erasable image forming material containing these components changes from the color developed state to the decolored state when heated or brought into contact with a solvent (alcohol or ketone).

The respective paper types described above have the following characteristics. (1) When plain paper having an image formed with an ordinary image forming material (toner or ink) is heated or brought into contact with a solvent, its reflection density (image density) does not change. (2) When plain paper having an image formed with an erasable image forming material is heated or brought into contact with a solvent, its image is erased and its reflection density is decreased greatly. (3) When thermosensible paper is heated or brought into contact with a solvent, its reflection density increases greatly.

Therefore, paper can be classified by discriminating how its reflection density changes upon being heated or applied with a solvent.

As the means for heating the paper, i.e., as the heater, a thermal printer head (TPH), a thermal bar, a laser beam head, a hot stamp, a heat roller, lamp heating, flash heating, hot-air heating, or the like is used.

As the means for supplying a solvent to the paper, an ink jet nozzle, a gravure roller, a spray nozzle, or the like is used.

As the means for detecting the reflection density of the paper, a detector (measurement unit for the reflected light intensity) for detecting light emitted by a light source, incident on the paper, and reflected by the paper is used. The optical detector can be a line sensor or serial sensor head. As the value of the reflection density, either one of the reflection density of one point of the paper, the reflection densities of a plurality of points on the entire surface or partial region of the paper, or an average of reflection densities of a plurality of points including high- and low-density portions, may be used. To prevent determination errors, it is preferable to detect the reflection densities of the two surfaces of paper.

According to the present invention, the reflection density of paper after heating the paper or supplying a solvent is compared with a predetermined reference value, or the reflection densities of paper before and after supplying a solvent are compared. When the reflection densities of paper before and after heating the paper or supplying a solvent are to be compared, reflection density detectors may be respectively provided before and after the heating means or solvent supplying means. Alternatively, one reflection density detector and a mechanism for changing the paper convey path may be provided so that the reflection densities are detected before and after heating the paper or supplying the solvent with one detector. After that, the paper is conveyed to the next stage. Comparison of the reflection densities is performed by using, e.g., a computer.

As the means for classifying the paper on the basis of the comparison result of the reflection densities, a mechanism such as a selector guide controlled by the reflection density comparing means is used.

When a transparent sheet for an OHP is to be classified in addition to the various types of paper, it is preferable to classify the transparent sheet first by measuring the light transmittance of the processing object, since the transparent sheet has a higher light transmittance than paper.

The respective types of classified paper are stored in temporary storage spaces. When storing the paper in the temporary storage spaces, a paper feed guide may be provided, so that the paper may be classified by discriminating the paper size with some means, e.g., by utilizing information concerning the light transmittance, and that the paper may be stored in the storage spaces corresponding to the respective paper sizes. The various types of classified paper may be continuously in-line processed with a secondary processing unit. An example of the secondary processing unit is an image erasing unit having a solvent tank for further improving the erased state of paper having an image formed with an erasable image forming material. Another example of the secondary processing unit is a thermosensible paper shredder, incineration unit, or the like.

FIGS. 1 to 4 show the flow charts of the paper classifying method according to the present invention. In FIGS. 1 to 4, a paper heating method is described. In place of heating the paper, a solvent may be supplied to the paper.

FIG. 1 shows the flow chart of the simplest paper classifying method. According to this method, the entire surface of the paper is heated (step S1). The reflection densities of a plurality of points of the paper after heating are measured, and their average is calculated (step S2). The measured reflection density is compared with a predetermined reference value, which is stored in a memory of a computer (step S3). As the reference value, an upper limit threshold and a lower limit threshold are used. If the reflection density is equal to the upper limit threshold or more, it is determined that an image is formed on at least a part of the paper surface. If the reflection density is equal to the lower limit threshold or less, it is determined that no image is formed. The upper and lower limit thresholds may be the same value. If the reflection density is equal to the upper limit threshold or more, the paper is determined as thermosensible paper, and is classified accordingly (step S4). If the reflection density is equal to the lower limit threshold or less, the paper is determined as reuse paper using an erasable image forming material, and is classified accordingly (step S5). If the reflection density falls within the range between these two thresholds, the paper is determined as plain paper using an ordinary image forming material, and is classified accordingly (step S6). This method requires only a few reflection density detecting operations, and accordingly has a high processing speed.

Figure 2:
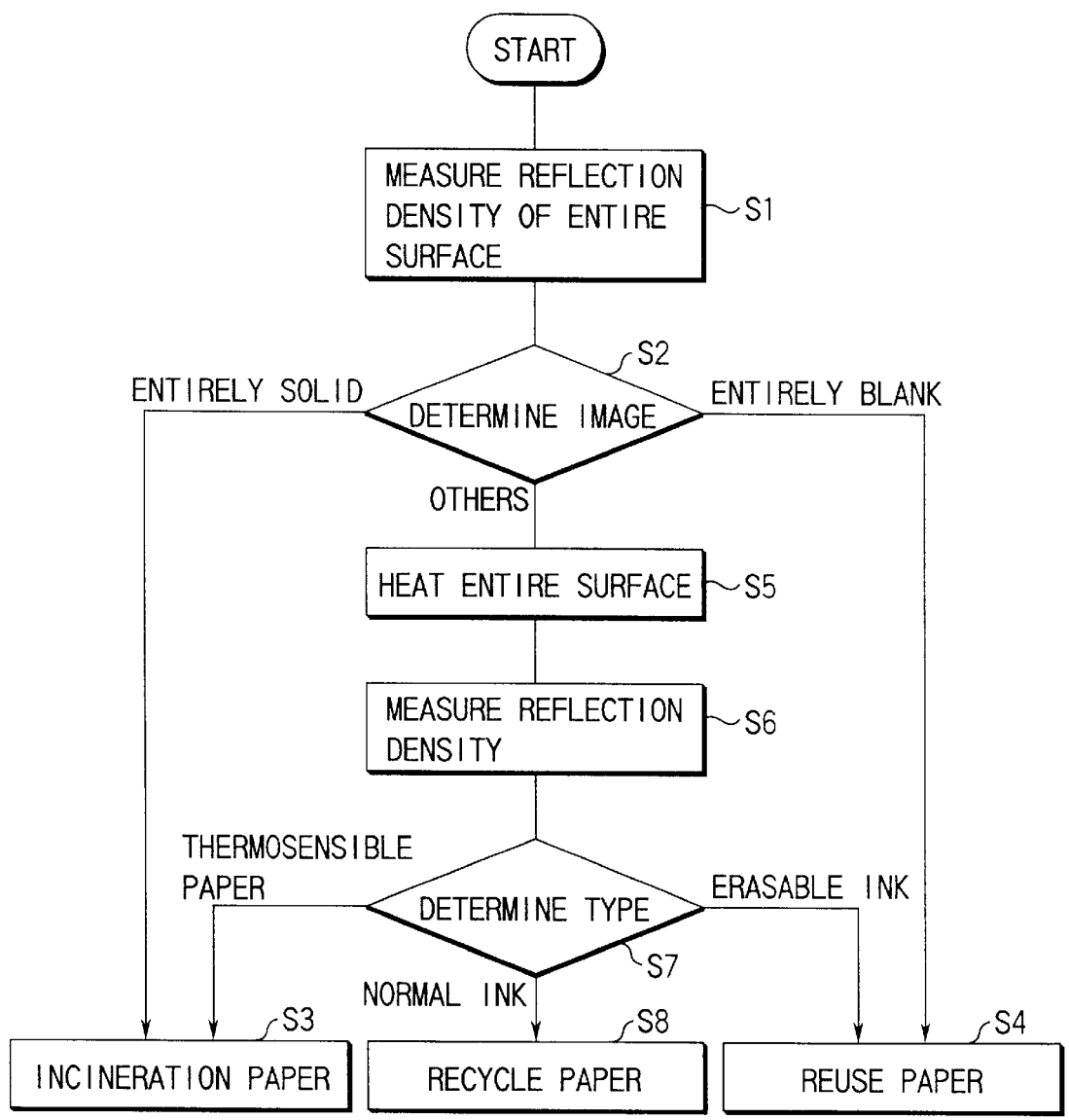
FIG. 2 is a flow chart showing another example of the paper classifying method according to the present invention.

With the method of FIG. 1, since entirely blank plain paper, entirely solid plain paper using an ordinary image forming material, and entirely solid thermosensible paper cannot be discriminated, paper of these types may be removed first. FIG. 2 shows the flow chart of such a paper classifying method. According to this method, first, the reflection density of the entire surface of paper is measured (step S1). The image is determined (step S2). If the image is an entirely solid image, the paper is classified as incineration paper (step S3). If the paper is entirely blank paper, it is classified as reuse paper (step S4). If thermosensible paper might be mixed in the reuse paper, the thermosensible paper may be further classified. To determine other types of paper, the entire surface of paper is heated in the same manner as in FIG. 1 (step S5). The reflection densities of a plurality of points of the paper are measured, and their average is calculated (step S6). The measured reflection density is compared with a predetermined reference value, which is stored in a memory of a computer, to determine the paper type (step S7). If the reflection density is equal to the upper limit threshold or more, the paper is determined as thermosensible paper, and is classified as incineration paper (step S3). If the reflection density is equal to the lower limit threshold or less, the paper is determined as reuse paper using an erasable image forming material, and is classified accordingly (step S4). If the reflection density falls within the range between these two thresholds, the paper is determined as plain paper using an ordinary image forming material, and is classified as recycle paper accordingly (step S8).

Figure 3:
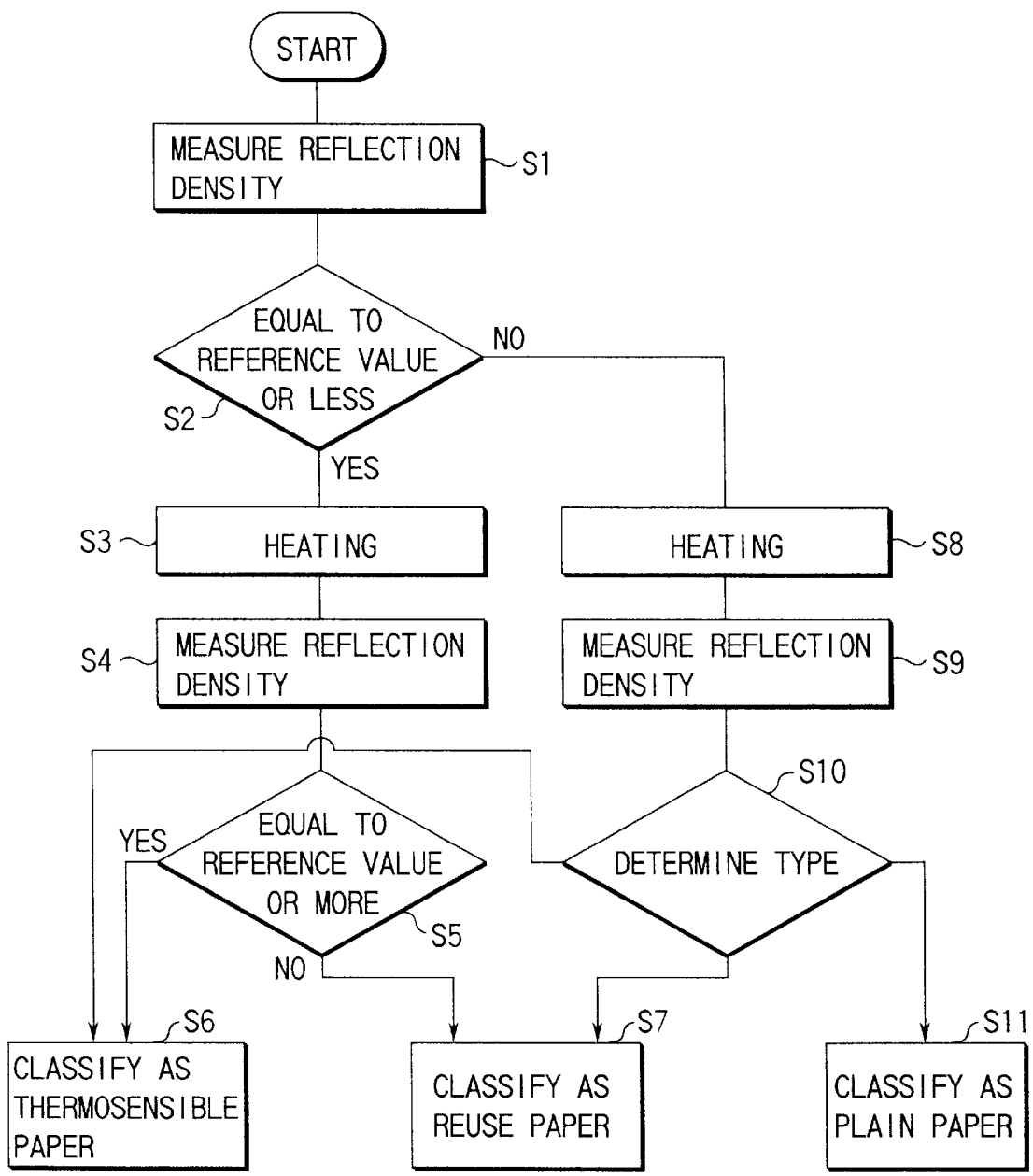
FIG. 3 is a flow chart showing still another example of the paper classifying method according to the present invention.

FIG. 3 shows the flow chart of a method of classifying paper by measuring the reflection densities before and after heating the paper. According to this method, first, the reflection densities of a plurality of points of the paper are measured, and their average is calculated (step Sl). The measured reflection density is compared with a predetermined reference value, which is stored in a memory of a computer (step S2). If the reflection value is equal to the reference value or less, it is determined that the paper is not formed with an image. In this case, the paper is heated (step S3). The reflection densities of the plurality of points of the paper are measured again, and their average is calculated (step S4). The measured reference density is compared with a predetermined reference value to determine the paper type (step S5). If the reflection density is equal to the reference value or more, the paper is determined as thermosensible paper, and is classified accordingly (step S6). If the reflection density is equal to the reference value or less, the paper is determined as reuse paper, and is classified accordingly (step S7).

In step S2, if the reflection density is not equal to the reference value or less, it is determined that the paper is formed with an image. In this case, the paper is heated (step S8). The reflection densities of the plurality of points of the paper are measured again, and their average is calculated (step S9). In the same manner as in FIG. 1, the measured reflection density is compared with the predetermined reference value to determine the paper type (step S10). If the reflection density is equal to the reference value or more, the paper is determined as thermosensible paper, and is classified accordingly (step S6). If the reflection density is equal to the reference value or less, the paper is determined as reuse paper using an erasable image forming material, and is classified accordingly (step S7). If the reflection density falls within the range between the two reference values, the paper is determined as plain paper using an ordinary image forming material, and is classified accordingly (step S11).

Alternatively, the reflection densities may be measured at a plurality of points of paper before and after heating, and the paper type may be determined in the following manner. More specifically, if a measurement point is present where the reflection density before heating is higher than the upper limit threshold (image-formed portion) and the reflection density after heating is lower than the lower limit threshold (image-nonformed portion), it is determined that the paper uses an erasable image forming material. If a measurement point is present where the reflection density before heating is lower than the lower limit threshold (image-nonformed portion) and the reflection density after heating is higher than the upper limit threshold (image-formed portion), the paper is determined as thermosensible paper. If a measurement point is present where the reflection density before heating is lower than the lower limit threshold (image-nonformed portion) and the reflection density after heating is also lower than the lower limit threshold (image-nonformed portion), or the reflection density before heating is higher than the upper limit threshold (image-formed portion) and the reflection density after heating is also higher than the upper limit threshold (image-formed portion), it is determined that the paper uses an ordinary image forming material.

Alternatively, the type of paper detected to have an image may be determined by comparing the averages of the reflection densities measured before and after heating. More specifically, if the reflection density after heating is lower than the reflection density before heating, it is determined that the paper uses an erasable image forming material. If the reflection density after heating is higher than the reflection density before heating, the paper is determined as thermosensible paper. If the reflection densities before and after heating show no change, it is determined that the paper uses an ordinary image forming material.

Figure 4:
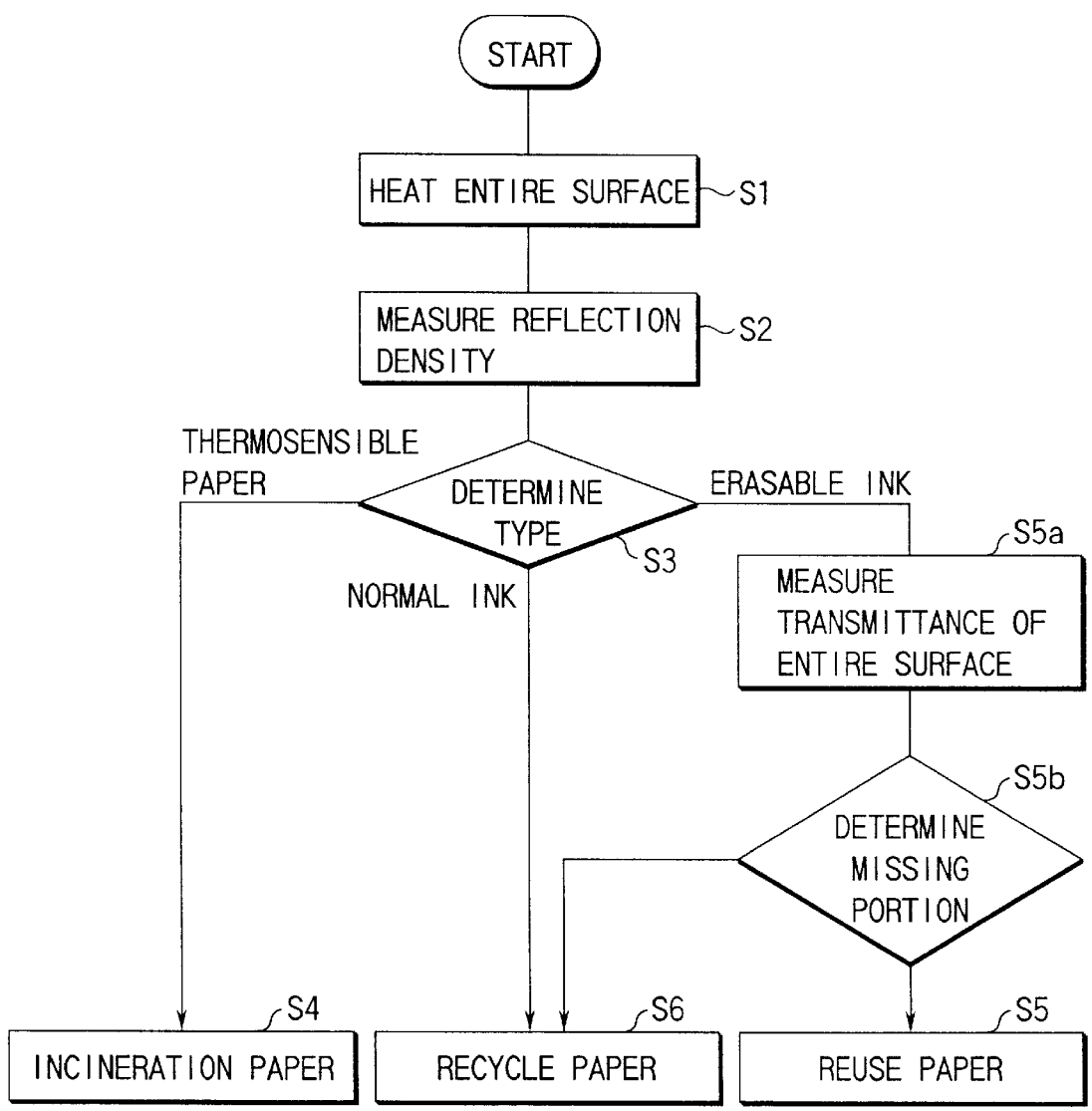
FIG. 4 is a flow chart showing still another example of the paper classifying method according to the present invention.

Reuse paper must not have a cut-off and must have a shape matching the standard. Hence, a paper classifying method as shown in FIG. 4 is preferably used for reuse paper. This method is almost the same as that of FIG. 1, except for the following respects. Assume that type determination on the basis of the measurement result of the reflection density (step S3) indicates that given paper uses an erasable image forming material. The light transmittance of the entire surface of this paper is measured (step S5a). The measurement result is utilized to discriminate presence/absence of a missing portion (cut-off or bent) (step S5b). Paper having no missing portion is classified as reuse paper (step S5), and paper having a missing portion is classified as recycle paper (step S6).

EXAMPLES

The examples of the present invention will be described.

Example 1

Figure 5:
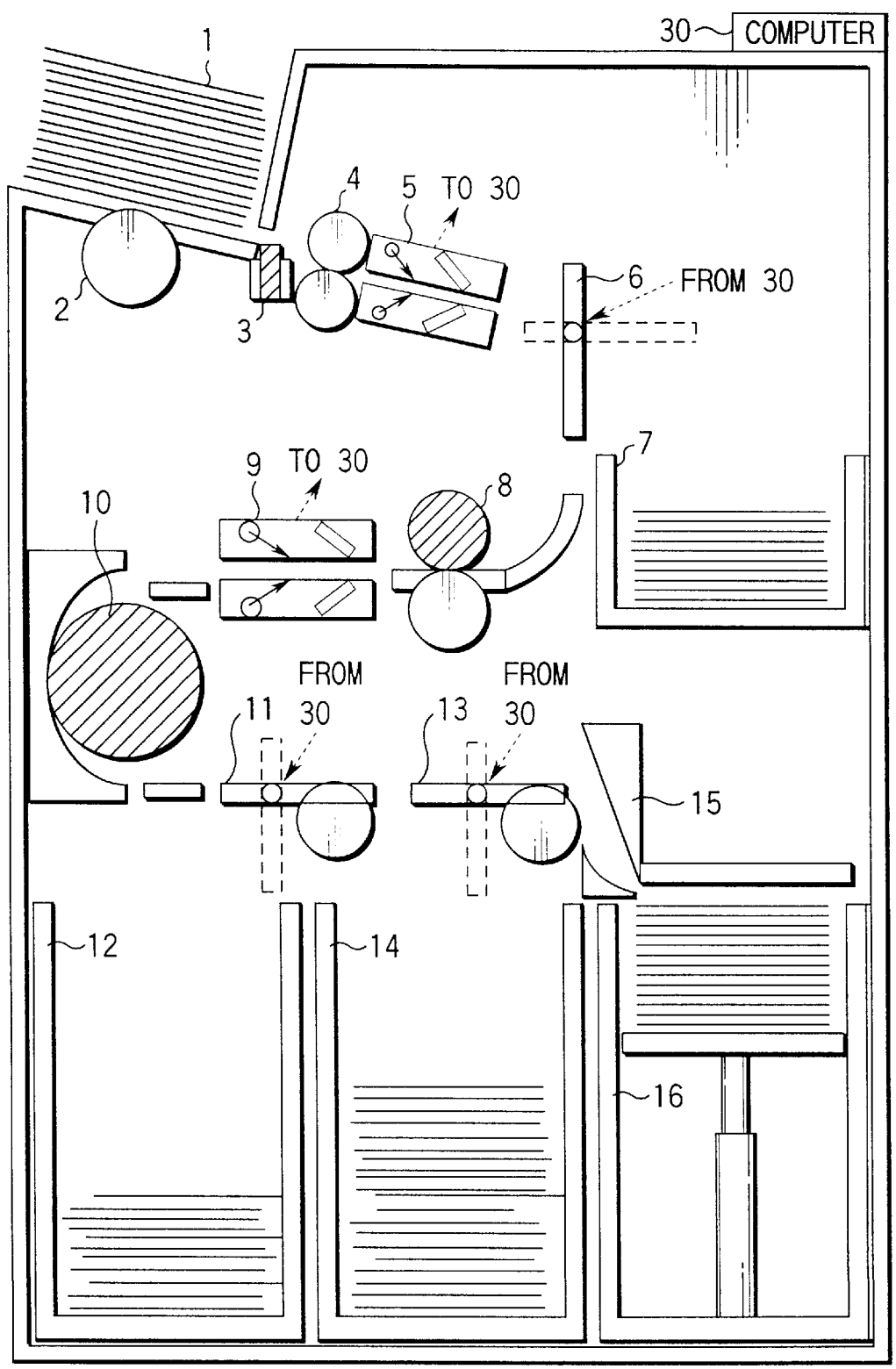
FIG. 5 is a view showing the arrangement of a paper classification apparatus according to the first example of the present invention.

FIG. 5 shows the arrangement of a paper classification apparatus according to an example of the present invention. Plain paper printed with an ordinary image forming material, plain paper printed with an erasable image forming material, thermosensible paper, and OHP transparent sheets are mixedly stacked on a sheet stacker 1. These paper objects are inserted into the classification apparatus one by one from the lowest one with a convey roller 2 arranged immediately under the sheet stacker 1. Presence/absence of paper inserted from the sheet stacker 1 is detected by a microswitch 3 near the inlet port. If it is determined that no paper is present, the overall apparatus is temporarily stopped. The paper can be detected by a non-contact detector, e.g., a photosensor or a capacity detector, in place of the microswitch.

The paper is sent to a first optical measurement system 5 through convey rollers 4. The light transmittance and the average reflection density of the two surfaces of this paper are measured. The light transmittance is compared, by a computer 30, with a reference value stored in a memory to determine whether the inserted object is a transparent sheet or paper. On the basis of the determination signal sent from the computer 30, a selector guide 6 is driven. If the light transmittance is higher than the reference value, the inserted object is determined as a transparent sheet, and is stored in a transparent sheet storage 7 by the selector guide 6. If the light transmittance is lower than the reference value, the inserted object is determined as paper, not a transparent sheet. The paper is sent toward heat rollers 8 by the selector guide 6, and its entire surface is heated. The average of the reflection densities of the two surfaces of the heated paper is measured by a second optical measurement system 9. The value of the reflection density of the paper after heating is compared, by the computer 30, with the value of the reflection density before heating, or with a predetermined reference value stored in the memory, to determine whether the paper is plain paper printed with an ordinary image forming material, plain paper printed with an erasable image forming material, or thermosensible paper. On the basis of the determination signal sent from the computer 30, selector guides 11 and 13 are driven. Thermosensible paper is stored in a thermosensible sheet storage 12 by the selector guide 11 through a sheet guide 10. Plain paper printed with an ordinary image forming material is stored in a recycle sheet storage 14 by the selector guide 13 through the sheet guide 10 and selector guide 11. Plain paper printed with an erasable image forming material is stored in a reuse sheet storage 16 through the sheet guide 10, the selector guides 11 and 13, and a sheet guide 15.

Alternatively, whether the paper has a missing portion may be determined by utilizing the value of the light transmittance obtained by the first optical measurement system 5. If the paper has a missing portion, the selector guide 13 may be driven to store the paper in the recycle sheet storage 14. After paper determination is ended (or after classification is ended), process for the following paper is started.

Example 2

Figure 6:
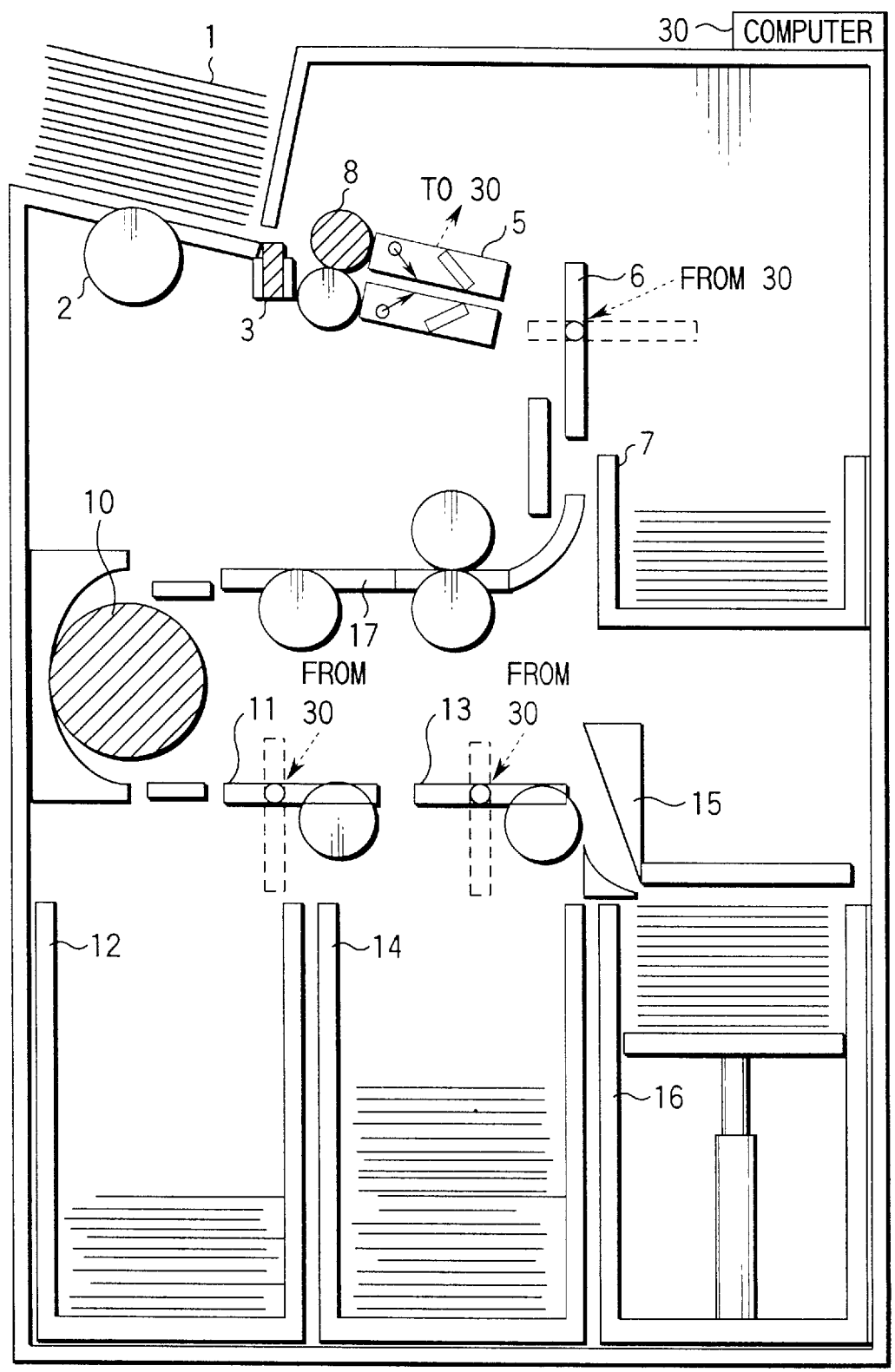
FIG. 6 is a view showing the arrangement of a paper classification apparatus according to the second example of the present invention.

FIG. 6 shows the arrangement of a paper classification apparatus according to another example of the present invention. This apparatus is simple; it compares the reflection density of the paper after heating with a reference value stored in a memory of a computer.

The mechanisms of a sheet stacker 1, a convey roller 2 under the sheet stacker 1, and a microswitch 3 are identical to those of Example 1 (FIG. 5). Paper conveyed into the apparatus is immediately entirely heated by heat rollers 8, and is sent to a first optical measurement system 5. The light transmittance and the average reflection density of the two surfaces of this paper are measured. The light transmittance is compared, by a computer 30, with the reference value stored in a memory to determine whether the inserted object is an OHP transparent sheet or paper. The value of the reflection density of the paper is compared, by the computer 30, with a predetermined reference value stored in the memory to determine whether the paper is plain paper printed with an ordinary image forming material, plain paper printed with an erasable image forming material, or thermosensible paper. On the basis of the determination signal sent from the computer 30, selector guides 6, 11, and 13 are driven. If the light transmittance is higher than the reference value, the inserted object is determined as a transparent sheet, and is stored in a transparent sheet storage 7 by the selector guide 6. If the light transmittance is lower than the reference value, the inserted object is determined as paper, not a transparent sheet. The paper is sent toward a convey roller 17 by the selector guide 6. After that, in the same manner as in the Example 1 (FIG. 5), thermosensible paper is stored in a thermosensible sheet storage 12. Plain paper printed with an ordinary image forming material is stored in a recycle sheet storage 14. Plain paper printed with an erasable image forming material is stored in a reuse sheet storage 16.

Example 3

Figure 7:
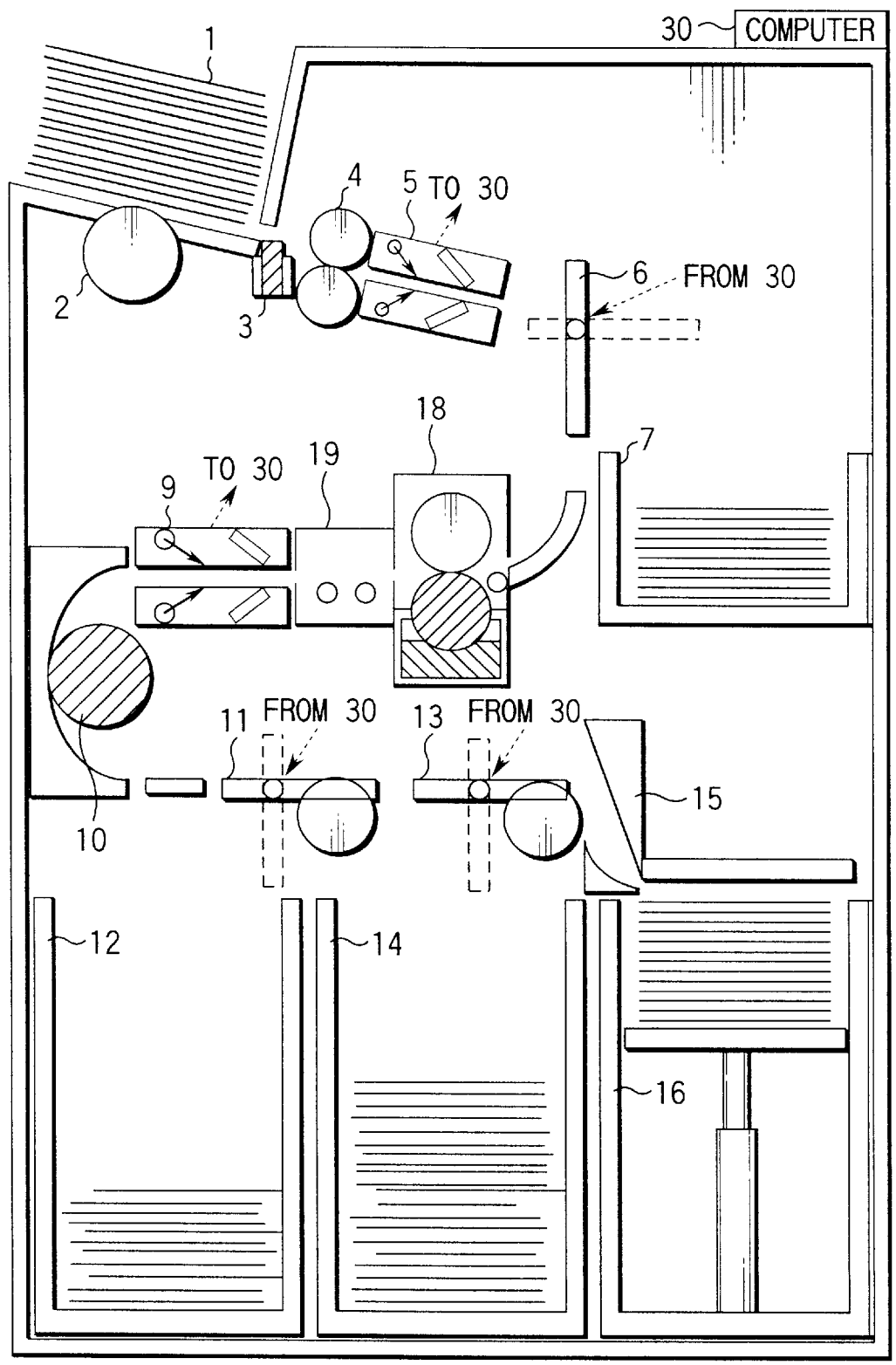
FIG. 7 is a view showing the arrangement of a paper classification apparatus according to the third example of the present invention.

FIG. 7 shows the arrangement of a paper classification apparatus according to still another example of the present invention. This apparatus has the same arrangement as that of FIG. 5 except for the following respects. Namely, a solvent coating unit 18 having gravure rollers is provided, in place of the heat rollers of FIG. 5, after a first optical measurement system 5. A dry room 19 is provided after the solvent coating unit 18 (before the second optical measurement system 9). The dry room 19 is connected to a solvent recovery mechanism (not shown). The solvent recovered by the solvent recovery mechanism is reutilized by the solvent coating unit 18. With this apparatus, paper can be classified in completely the same manner as in the apparatus of FIG. 5.

Example 4

Figure 8:
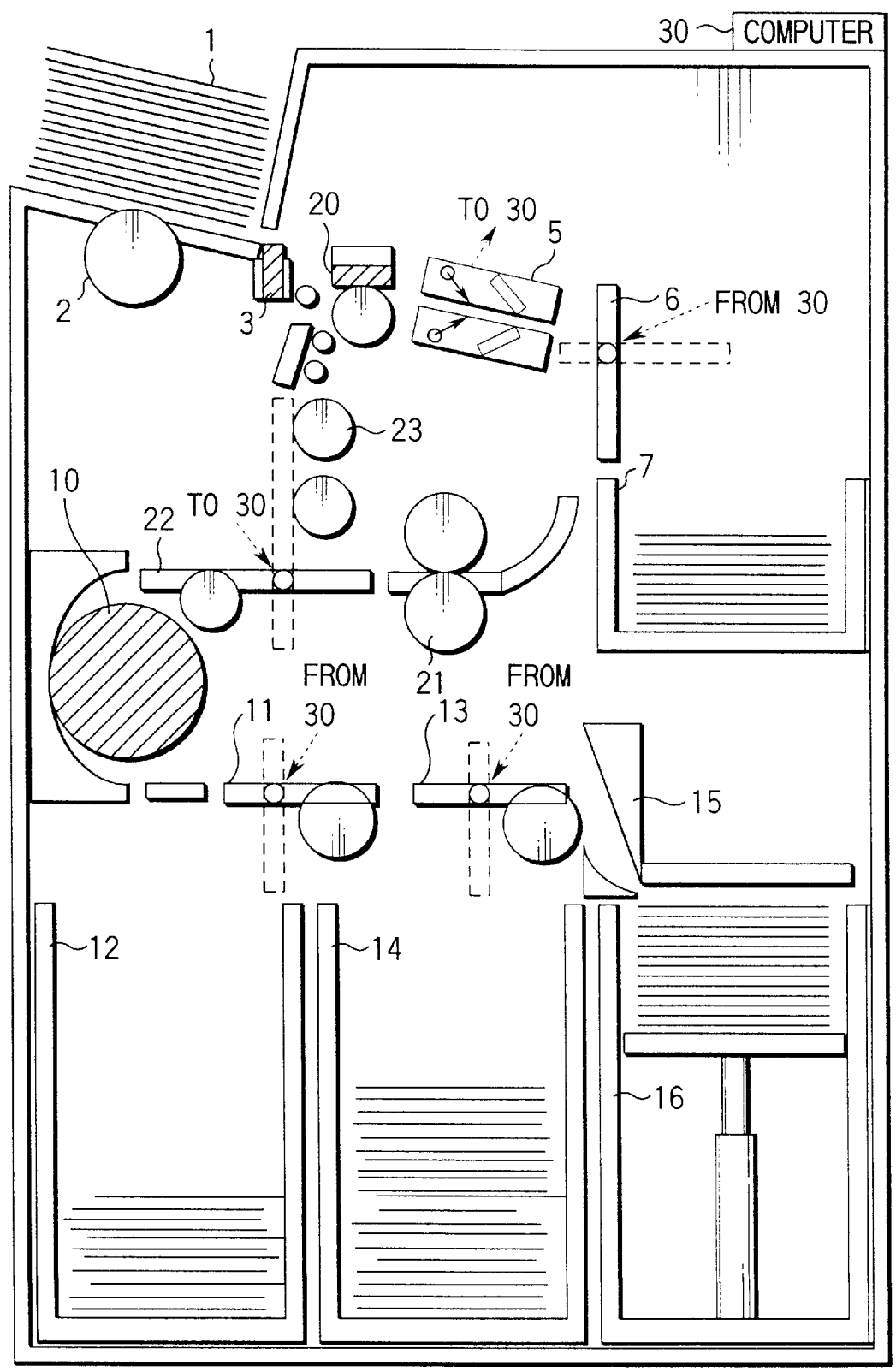
FIG. 8 is a view showing the arrangement of a paper classification apparatus according to the fourth example of the present invention.

FIG. 8 shows the arrangement of a paper classification apparatus according to still another example of the present invention. This apparatus uses one optical measurement system, and measures the reflection density by sending paper to an optical measurement system before and after heating.

The mechanisms of a sheet stacker 1, a convey roller 2 under the sheet stacker 1, and a microswitch 3 are identical to those of Example 1 (FIG. 5). First, paper conveyed into the apparatus is sent to a first optical measurement system 5 without being pressed by a thermal bar 20. The light transmittance and the average reflection density of the two surfaces of this paper are measured. The light transmittance is compared, by a computer 30, with a reference value stored in a memory to determine whether the inserted object is an OHP transparent sheet or paper. On the basis of the determination signal sent from the computer 30, a selector guide 6 is driven. If the light transmittance is higher than the reference value, the inserted object is determined as a transparent sheet, and is stored in a transparent sheet storage 7 by the selector guide 6. If the light transmittance is lower than the reference value, the inserted object is determined as paper, not an OHP transparent sheet. The paper is sent toward convey rollers 21 by the selector guide 6. Then, the direction of the paper convey path is changed by a selector guide 22 responded to a driving signal sent from the computer 30. The paper is conveyed by convey rollers 23 and is pressed and heated by the thermal bar 20. After that, the paper is sent to the first optical measurement system 5, and the light transmittance and the average reflection density of the two surfaces of the paper are measured. The value of the reflection density of the paper after heating is compared, by the computer 30, with the value of the reflection density before heating, or with a predetermined reference value stored in the memory, to determine whether the inserted object is plain paper printed with an ordinary image forming material, plain paper printed with an erasable image forming material, or thermosensible paper. On the basis of the determination signal sent from the computer 30, selector guides 11 and 13 are driven. After that, the paper is fed through a convey path similar to that of Example 1 (FIG. 5). Thermosensible paper is stored in a thermosensible sheet storage 12. Plain paper printed with an ordinary image forming material is stored in a recycle sheet storage 14. Plain paper printed with an erasable image forming material is store in a reuse sheet storage 16.

Example 5

Figure 9:
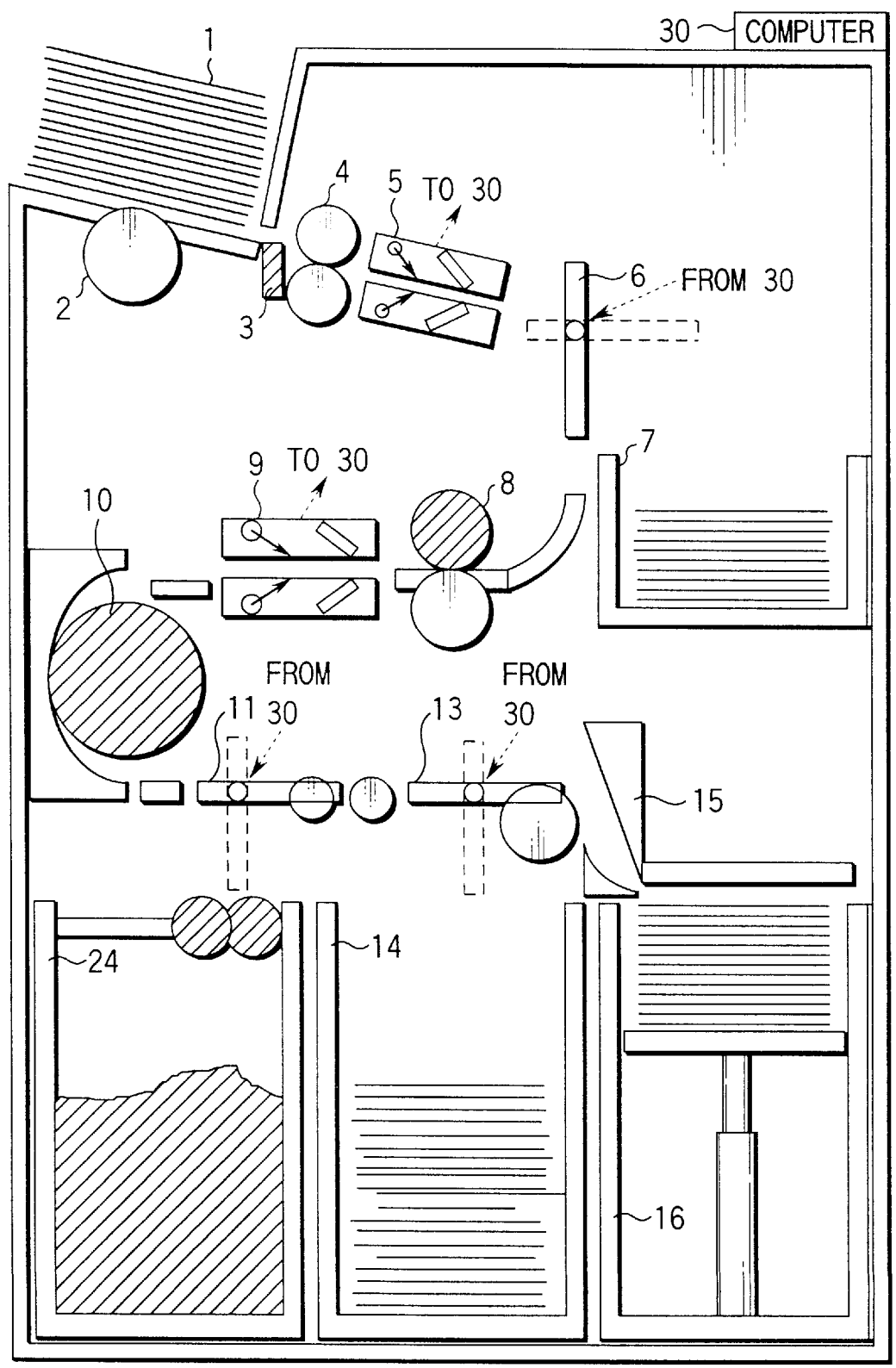
FIG. 9 is a view showing the arrangement of a paper classification apparatus according to the fifth example of the present invention.

FIG. 9 shows the arrangement of a paper classification apparatus according to still another example of the present invention. This apparatus has a processing mechanism for classified paper, and its basic arrangement is almost identical to that of the apparatus shown in FIG. 5.

Thermosensible paper is an incompatible article that cannot be reused or recycled, and cannot accordingly be reutilized other than as fuel or a packaging medium. In the apparatus shown in FIG. 9, in consideration of keeping confidentiality of documents as well, a shredder 24 is provided in place of the thermosensible sheet storage 12 of FIG. 5 to continuously shred classified thermosensible paper.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A paper classification apparatus comprising:
   a heater configured to heat paper;
   a detector configured to detect a reflection density of the paper after being heated;
   a computer configured to compare the detected reflection density of the paper with a predetermined reference value; and
   a selector guide configured to classify the paper on the basis of a comparison result of the reflection density.

2. The apparatus according to claim 1, wherein said detector measures the reflection density of an entire surface of the paper.

3. The apparatus according to claim 1, wherein said detector measures reflection densities of a plurality of points on the paper.

4. The apparatus according to claim 1, wherein said computer determines the paper as thermosensible paper when the reflection density is not less than a predetermined upper limit threshold, as plain paper using an erasable image forming material when the reflection density is not more than a lower limit threshold, and as plain paper using an ordinary image forming material when the reflection density falls on a value between the upper and lower limit thresholds.

5. A paper classification apparatus comprising:
   a first detector configured to detect a reflection density of paper;
   a heater configured to heat the paper;
   a second detector configured to detect the reflection density of the paper before and after being heated;
   a computer configured to compare reflecting densities of the paper before and after being heated; and
   a selector guide configured to classify the paper on the basis of a comparison result of the reflection densities.

6. The apparatus according to claim 5, comprising:
   one detector that functions as said first and second detectors, and
   a mechanism configured to control a convey path for the paper after being transmitted through said heater.

7. The apparatus according to claim 6, wherein said detector measures the reflection density of an entire surface of the paper.

8. The apparatus according to claim 6, wherein said detector measures reflection densities of a plurality of points on the paper.

9. The apparatus according to claim 6, wherein said computer determines the paper as plain paper using an erasable image forming material when the reflection density after being heated is lower than the reflection density before being heated, as thermosensible paper when the reflection density after being heated is higher than the reflection density before being heated, and as plain paper using an ordinary image forming material when no change is found between the reflection densities before and after being heated.

10. A paper classification apparatus comprising:
    a solvent supply unit configured to supply a solvent to paper;
    a detector configured to detect a reflection density of the paper after being supplied with the solvent;
    a computer configured to compare the detected reflection density of the paper with a predetermined reference value; and
    a selector guide configured to classify the paper on the basis of a comparison result of the reflection density.

11. The apparatus according to claim 10, wherein said detector measures the reflection density of an entire surface of the paper.

12. The apparatus according to claim 10, wherein said detector measures reflection densities of a plurality of points on the paper.

13. The apparatus according to claim 10, wherein said computer determines the paper as thermosensible paper when the reflection density is not less than a predetermined upper limit threshold, as plain paper using an erasable image forming material when the reflection density is not more than a lower limit threshold, and as plain paper using an ordinary image forming material when the reflection density falls on a value between the upper and lower limit thresholds.

14. A paper classification apparatus comprising:
    a first detector configured to detect a reflection density of paper;
    a solvent supply unit configured to supply a solvent to the paper;

a second detector configured to detect the reflection density of the paper after being supplied with the solvent;

a computer configured to compare reflection densities of the paper before and after being supplied with the solvent; and a selector guide configured to classify the paper on the basis of a comparison result of the reflection densities.

15. The apparatus according to claim 14, comprising:

one detector that functions as said first and second detectors; and a mechanism configured to control a convey path for the paper after being transmitted through said solvent supply unit.

16. The apparatus according to claim 15, wherein said detector measures the reflection density of an entire surface of the paper.

17. The apparatus according to claim 15, wherein said detector measures reflection densities of a plurality of points on the paper.

18. The apparatus according to claim 14, wherein said computer determines the paper as plain paper using an erasable image forming material when the reflection density after being supplied with the solvent is lower than the reflection density before being supplied with said solvent, as thermosensible paper when the reflection density after being supplied with the solvent is higher than the reflection density before being supplied with the solvent, and as plain paper using an ordinary image forming material when no change is found between the reflection densities before and after being supplied with the solvent.

* * * * *